United States Patent [19]

Hahn et al.

[11] 4,168,915

[45] Sep. 25, 1979

[54] ROTARY DRUM

[75] Inventors: Volker Hahn, Leinfelden; Gustav Moritz, Neuhausen, both of Fed. Rep. of Germany; Paul F. Jetter, Vienna, Austria

[73] Assignee: Ed. Züblin Aktiengesellschaft, Stuttgart, Fed. Rep. of Germany

[21] Appl. No.: 819,250

[22] Filed: Jul. 27, 1977

[51] Int. Cl.² .............................................. B01F 9/06
[52] U.S. Cl. ............................ 366/105; 110/246; 366/107; 366/180; 366/228
[58] Field of Search ............... 366/220, 233, 224, 228, 366/105, 107, 225, 180; 432/110, 248, 119, 110.1 A; 110/14

[56] References Cited

U.S. PATENT DOCUMENTS

| | | | |
|---|---|---|---|
| 1,188,567 | 6/1916 | Singer | 432/110 |
| 1,534,180 | 4/1925 | Komarek | 432/110 |
| 1,898,776 | 2/1933 | Horn | 432/110 |
| 2,288,372 | 6/1942 | Rump | 432/119 |
| 2,633,347 | 3/1953 | Heyman | 432/119 |

*Primary Examiner*—Robert W. Jenkins
*Attorney, Agent, or Firm*—Becker & Becker

[57] ABSTRACT

A rotary drum for treating, especially upgrading, waste material, which includes a cylindrical mantle with an inlet and an outlet respectively provided at opposite ends of the drum and which is provided with annular guides for supporting the drum on stationary supports. The inner wall of the drum is made of concrete.

7 Claims, 9 Drawing Figures

ROTARY DRUM

The present invention relates to a rotary drum for treating, especially upgrading, waste material. Rotary drums have become known for this purpose as disclosed, for instance, in German Pat. No. 1 592 612. The waste material obtained from households and industrial plants is introduced into such drum in crushed or uncrushed condition, and clearing or settling slurry and water are added while the drum is slowly rotated about its longitudinal axis so that the waste material is subjected to further diminution and intermixing. The rotary drum may be operated in a continuous manner or the waste material may be introduced into the drum in batches. The mixture passes through the drum in the direction towards its outlet end while pure oxygen or air or air enriched with oxygen is intermittently blown into the drum. Furthermore water may be added to the contents in the drum in a controlled manner which water, depending on the properties of the mixture, is preheated. Under the influence of the humidity, the oxygen of the air and its self-heating, a fermentation process takes place, and the metabolic products generated in this connection are withdrawn from the drum while, in view of the continuous rotation of the drum, the mixture is mechanically homogenized. From the waste material there will thus be obtained due to the rotting process a compost which can be used as soil improving substance and fertilizer or which by a further treatment can be converted in such a way that it will be suitable as starting material for industrial products.

The rotary drums consist customarily of a steel mantle which, in view of its thin wall, is insulated on the outside. The insulation is interrupted in the region of the support of the drum, and for driving the drum there is additionally provided on the steel mantle a gear ring meshing with a driving gear. In the area of the support and of the drive, the steel mantle must additionally be reinforced by wall metal sheets and by reinforcing metal sheets.

The inner wall of the steel mantle is liable to be attacked by corrosion caused by the aggressive mixture and therefore has to be protected. To this end it is known to line the inner wall of the mantle, which consists of approximately 10 mm thick sheet metal, with metal plates having a thickness of 5 mm, or to provide the mantle with metallic ribs or fins between which a protective layer of felted or compacted waste material will deposit (German Auslegeschrift No. 1 297 120). In spite of this measure a frequent servicing of the drum is necessary because the metal plates provided for the protection of the mantle likewise wear and corrode so that a layer of the components of the waste material can grow in an uncontrolled manner.

It is, therefore, an object of the present invention to provide a rotary drum of the above described general type which will be safe in operation in spite of a minimum of servicing time.

This object and other objects and advantages of the invention will appear more clearly from the following specification in connection with the accompanying drawings, in which.

Figure 7:
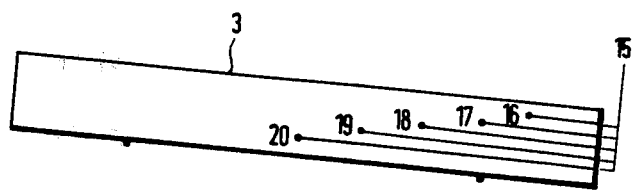

FIG. 7 diagrammatically illustrates the distribution of the pipe lines over the length of the rotary drum.

Figure 8:
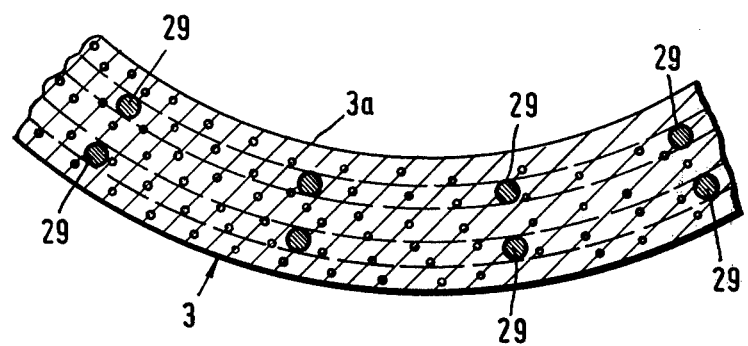

FIG. 8 is a fragmentary view of structure including steel inserts according to the present invention.

Figure 9:
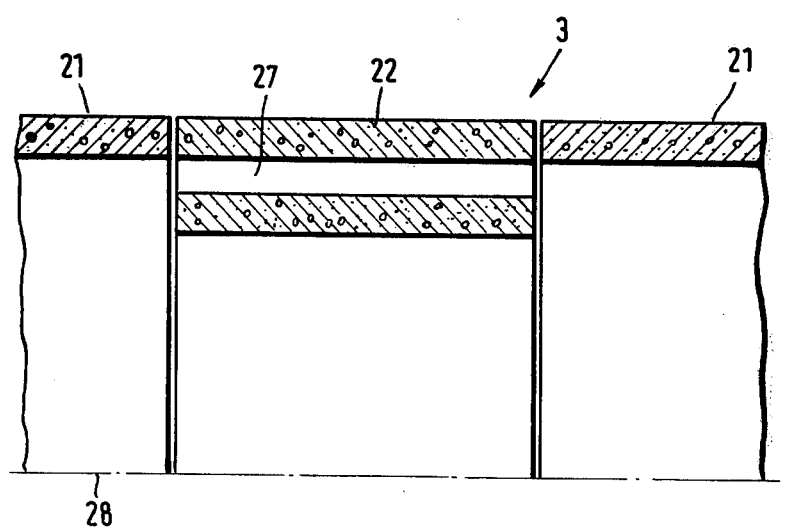

FIG. 9 is a fragmentary plan view of structure having bores according to the present invention.

The rotary drum according to the present invention is characterized primarily in that the inner wall of the drum mantle consists of concrete.

The surface consisting of concrete of the inner wall of the drum mantle has the advantage that the drum will not be attacked by the rotting process of the waste material and the aggressive substances generated in connection therewith so that servicing work for correcting corrosion damage will be eliminated.

Furthermore, the concrete surface of the inner wall of the mantle is relatively rough in comparison to that of a steel mantle so that the mixture of the waste material will be continuously carried along by the drum mantle and will be conveyed in the direction toward the outlet.

A preferred embodiment of the rotary drum according to the invention consists in that the drum mantle of concrete is made self-supporting. As a result thereof the mantle can in a favorable manner be manufactured from pre-fabricated concrete elements of high precision. Furthermore, such a drum is non-sensitive to explosions which may occur in the interior of the drum due to the formation of gases.

According to another embodiment of the rotary drum of the invention, the drum mantle is designed as a pipe which has its inner surface lined with concrete while its supporting mantle part is made of metal, such as steel or aluminum. Also such a drum is corrosion-resistant. The lining may consist of sprayed concrete which has to be applied as a coat to the inner wall of the pipe by spraying. Rotary drums of this design may likewise be composed of pre-fabricated elements.

Figure 1:
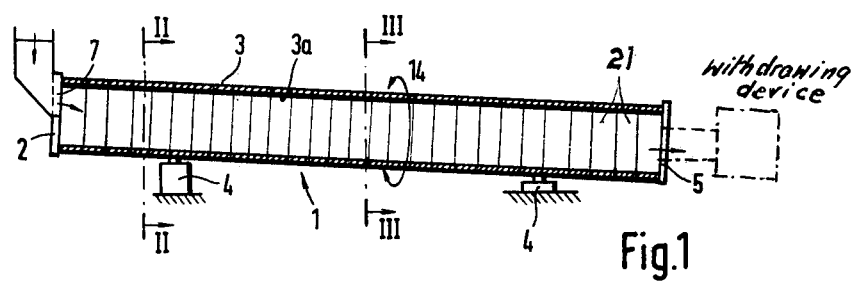
FIG. 1 represents an axial section through a rotary drum according to the invention.
Figure 2:
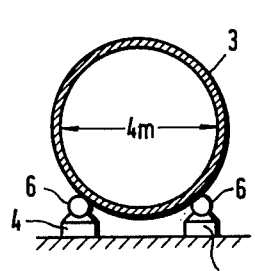
FIG. 2 represents a cross section along the line II—II of FIG. 1.

Referring now to the drawings in detail, the rotary drum 1 shown in FIG. 1 has a mantle 3 which consists of concrete and which is composed (not illustrated) of individual pre-fabricated pipe sections. The inner wall 3a of the drum mantle therefore likewise consists of concrete. On one of its end faces, the drum mantle is closed by a cover 2 which has an inlet opening 7. The other end face of the drum mantle is likewise closed by a cover 5 in which there is provided an opening for connection with a withdrawing device (not shown). The length of the rotary drum amounts to about 30 m while its inner diameter amounts to about 4 m. The drum mantle rests on rollers 6 which pertain to supports 4 and which are driven. The rollers 6 are provided with a friction coating so that the concrete mantle is frictionally driven. The drive is reversible; therefore, the drum can alternately be driven in either direction of the double arrow 14. In the region of the support, annular profile rails 11 are connected to the outer wall of the drum mantle which rails secure the drum against displacement in axial direction. The outer wall of the drum mantle is on both sides of the support covered by an insulating layer 10. An insulation is, however, not necessary under all circumstances.

Figure 5:
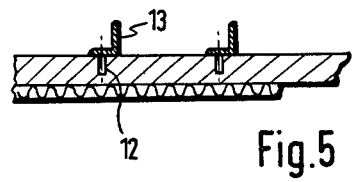
FIG. 5 illustrates a cutout of the axial section of FIG. 1 in the central region of the drum, but on a larger scale than that of FIG. 1.

The outlet in the cover 5 may be in the form of a centric or eccentric outlet opening. However, in a manner known per se, for the coarse screening of the compost to be discharged, a cylindrical screen may be provided which forms the end of the drum. As will be seen from FIG. 5, holding means 12 are embedded into the concrete of the drum mantle. Inserts 13 are exchangeably connected to the holding means 12. These inserts consist of profiled rails or fins but may also have the design of vanes in order to aid the feeding or conveying of the mixture in the outlet direction. Such inserts accelerate the homogenization of the waste-material-clearing slurry-mixture. Generally, the drum is operated with a degree of filling of from 50 to 80%.

Figure 3:
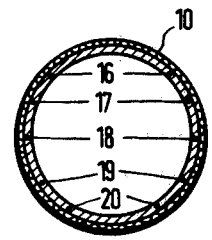
FIG. 3 is a cross section taken along the line III—III of FIG. 1.
Figure 4:
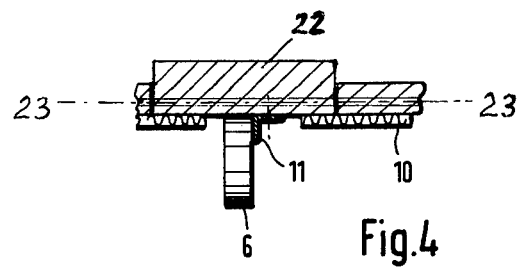
FIG. 4 represents a cutout of the axial section according to FIG. 1 within the region of the supports, but on a larger scale than that of FIG. 1.
Figure 6:
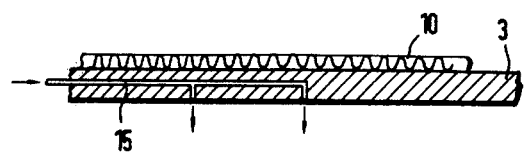
FIG. 6 represents a cutout of the drum mantle with pipe lines embedded therein.

As will be evident from FIGS. 3, 6 and 7, pipe lines 16 to 20 are embedded into the concrete of the drum mantle. These pipe lines extend in the longitudinal direction of the drum mantle and are arranged on each side of the drum mantle in pairs as shown in FIG. 3. As will likewise be evident from FIG. 3, the pipe lines of each pair located opposite to each other have the same length, and the pipe lines of each pair of pipes have a different length from that of the following pair of pipes. The ends of the pipe lines lead into the interior of the drum (FIG. 6). However, also a plurality of outlets may be distributed over the length of each pipe line.

Air, oxygen or oxygen enriched air is intermittently blown into these pipe lines, and at the inlet end there is provided a suction device (not shown) so that the mixture of waste material is passed through by the air-gas-mixture in a direction counter to its feeding direction according to the counter current principle. It has also proved advantageous to blow-in the air, oxygen or air enriched with oxygen directly at the discharge end on the cover 5.

Since the drum mantle of concrete is also weather resistant, the rotary drum can be installed outside. In this instance the two ends of the drum should be protected by covers or the like.

If desired, also two rotary drums may be provided so that the prepared compost can be treated a second time, so that a post-rotting in a compost stack or pile will not be necessary or that the post-rotting time can be reduced in conformity with the respective desired quality of the compost. The individual pipe sections from which the mantle is composed may have a length of from 4 to 6 m. The wall thickness may amount to from 15 to 20 cm while intermediate pipe sections with greater wall thickness may be provided which have bores therethrough for receiving tensioning members by means of which the pipe sections can be clamped together. The drum mantle can be supported within the region of the thicker pipe sections. Enveloping pipes embedded into the concrete receive the tensioning members by means of which the pipe sections will then be clamped together.

For the sake of completeness, it is noted that the mantle 3 is composed of pipe sections 21 rigged together in the axial direction of said drum along axis 23. Some of the pipe sections 22 have a greater wall thickness than the remainder of the drum mantle 3 and are provided with bores for receiving clamping elements along axis 23 to rig the pipe sections together. The outer wall of the drum mantle 3 consists of a material having a high coefficient of friction for example $0.5 \leq \mu m < 1.0$, especially for concrete as the material and supported directly upon the rollers or supports 6 which are driven and provided with a friction layer for instance of rubber. The inner wall $3a$ of the drum mantle 3 is provided with a corrosion-protective layer, for instance sprayed concrete (Spritzbeton) or synthetic concrete or synthetic material.

FIG. 8 shows reinforcing steel inserts 29 in the form of two steel rod lattices which are arranged in overlying spaced relationship in a plane perpendicular to the axis of the drum mantle 3. FIG. 9 shows bores 27 which are arranged parallel to the drum mantle axis 28 in an intermediate pipe section 22 being faced in end-to-end relationship by pipe sections 21 without bores 27.

It is, of course, to be understood that the present invention is by no means limited to the specific showing in the drawings but also comprises any modifications within the scope of the appended claims.

What we claim is:

1. A rotary drum for upgrading waste, comprising a cylindrical mantle having inlet and outlet means respectively provided at opposite ends of said drum, and bearing means stationarily arranged with regard to said drum for supporting the latter, said drum mantle being of concrete having pipe lines embedded therein which extend in the direction of the longitudinal axis of said drum and have a mouth leading into the interior of said drum, said drum mantle further being composed of pipe sections rigged together in the axial direction of said drum, the inner wall of said drum mantle forming the inner wall of said drum and having embedded therein holding means for insert means, whereas the outer wall of said drum mantle directly rests on said bearing means, which include roller means provided with a friction liner.

2. A rotary drum according to claim 1, in which some of said pipe sections have a greater wall thickness than the remainder of said drum mantle and are provided with bores for receiving clamping elements to rig said pipe sections together.

3. A rotary drum according to claim 1, in which said drum mantle comprises reinforcing steel inserts.

4. A rotary drum according to claim 1, in which said holding means are adapted to receive and secure ribs.

5. A rotary drum according to claim 1, in which the mouths of said pipe lines are respectively spaced from the axial direction of said drum, said pipe lines having inlets located at the outlet end of said drum.

6. A rotary drum according to claim 1, in which said pipe lines are arranged in pairs uniformly distributed over the drum circumference.

7. A rotary drum according to claim 6, in which the two pipe lines of each pair of pipe lines are located opposite to each other.

* * * * *

UNITED STATES PATENT AND TRADEMARK OFFICE
CERTIFICATE OF CORRECTION

PATENT NO. : 4168915
DATED : 25 September 1979
INVENTOR(S) : Volker Hahn, Gustav Moritz, and Paul Fritz Jetter It is certified that error appears in the above-identified patent and that said Letters Patent are hereby corrected as shown below:

[30]   Foreign Application Priority Data

Jul. 30, 1976 [DE] Fed. Rep. of Germany...2634220

Signed and Sealed this

Twenty-seventh Day of May 1980

[SEAL]

*Attest:*

SIDNEY A. DIAMOND

*Attesting Officer*   *Commissioner of Patents and Trademarks*